United States Patent
McCauley

(10) Patent No.: US 6,593,569 B2
(45) Date of Patent: Jul. 15, 2003

(54) COLLISIONAL GAS DELIVERY APPARATUS AND METHOD

(75) Inventor: Edward B. McCauley, Cedar Park, TX (US)

(73) Assignee: Thermo Finnigan LLC, San Jose, CA (US)

(*) Notice: Subject to any disclaimer, the term of this patent is extended or adjusted under 35 U.S.C. 154(b) by 210 days.

(21) Appl. No.: 09/780,664

(22) Filed: Feb. 8, 2001

(65) Prior Publication Data

US 2002/0104965 A1 Aug. 8, 2002

(51) Int. Cl.[7] .......................... H01J 49/00; B01D 59/44
(52) U.S. Cl. ...................... 250/288; 250/281; 250/282; 250/283
(58) Field of Search ................... 250/310, 281, 250/282, 285, 288, 289

(56) References Cited

U.S. PATENT DOCUMENTS

| | | | | |
|---|---|---|---|---|
| 3,853,144 A | * | 12/1974 | Whelan | 137/883 |
| 3,933,047 A | * | 1/1976 | Fowler | 250/288 |
| 5,352,892 A | * | 10/1994 | Mordehai et al. | 250/288 |
| 5,504,329 A | * | 4/1996 | Mann et al. | 250/288 |
| 5,597,467 A | * | 1/1997 | Zhu et al. | 204/603 |
| 5,621,180 A | * | 4/1997 | Simon et al. | 73/864.52 |
| 5,739,530 A | * | 4/1998 | Franzen et al. | 250/288 |
| 5,811,800 A | * | 9/1998 | Franzen et al. | 250/288 |
| 5,859,433 A | * | 1/1999 | Franzen | 250/292 |
| 5,869,344 A | * | 2/1999 | Linforth et al. | 436/173 |
| 6,140,639 A | * | 10/2000 | Gusev et al. | 250/288 |
| 2001/0030285 A1 | * | 10/2001 | Miller et al. | 250/288 |
| 2002/0092979 A1 | * | 7/2002 | McCauley et al. | 250/282 |

FOREIGN PATENT DOCUMENTS

| EP | 1225446 A2 | * | 7/2002 | ........ G01N/33/00 |
|---|---|---|---|---|

* cited by examiner

Primary Examiner—John R. Lee
Assistant Examiner—Bernard Souw
(74) Attorney, Agent, or Firm—Dorsey & Whitney LLP

(57) ABSTRACT

Apparatus and method for delivering collisional gas to a mass spectrometer at a desired flow rate which employs a capillary flow restrictor having internal diameter and length selected to provide the desired flow rate.

3 Claims, 1 Drawing Sheet

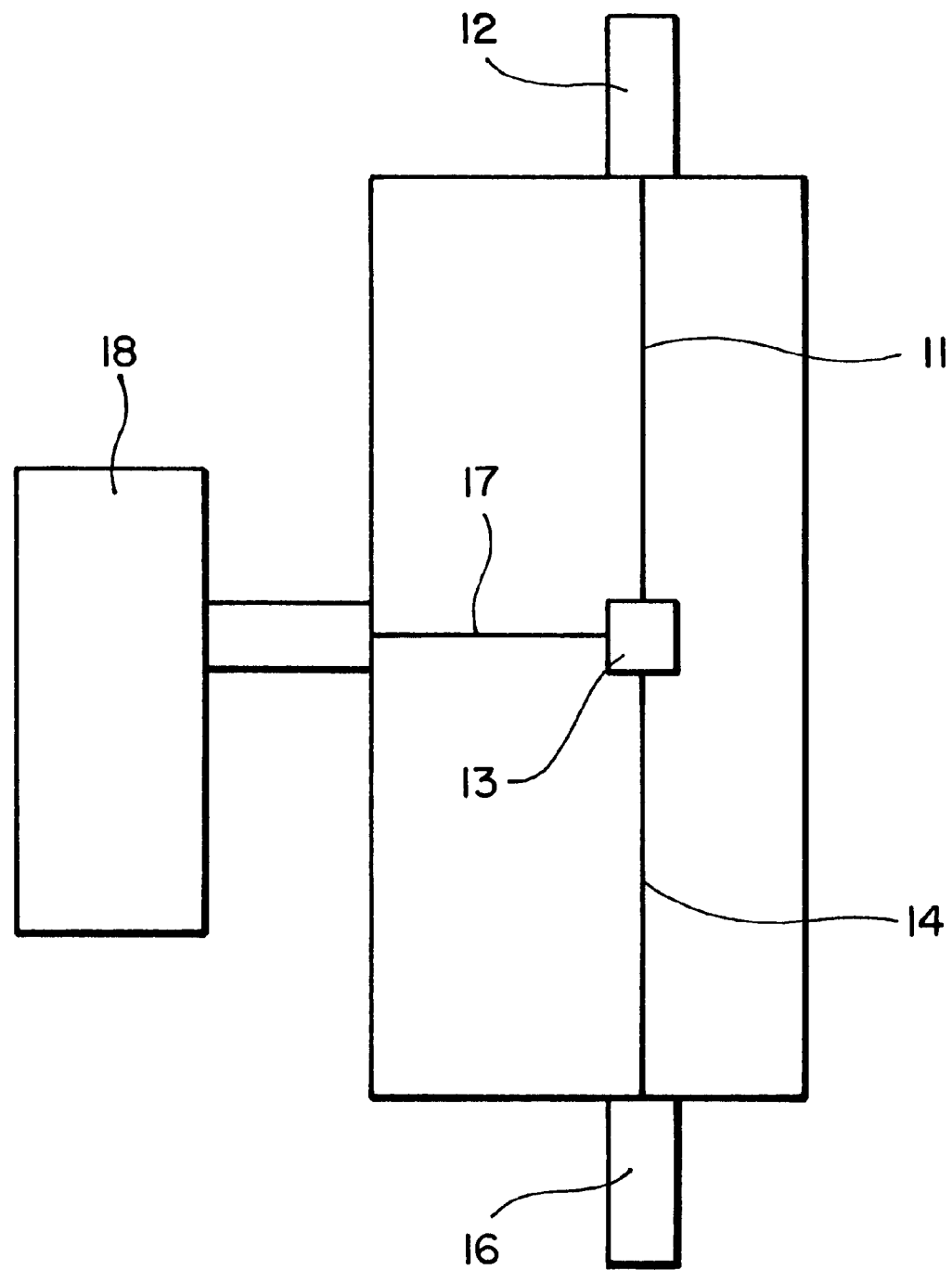

COLLISIONAL GAS DELIVERY APPARATUS AND METHOD

BRIEF DESCRIPTION OF THE INVENTION

This invention relates generally to an apparatus for delivering dry collisional damping gas to a mass spectrometer and method, and more particularly to an apparatus which is continuously purged.

BACKGROUND OF THE INVENTION

Inert gas such as helium is employed for collisional damping of ions within the operating region of mass spectrometers such as in the ion trapping region of an ion trap mass spectrometer. In order to prevent unwanted water-induced ion molecule reactions from occurring within an ion trap, the damping gas must be as free as possible from residual water vapor. Traditional damping gas inlet systems for collisional damping of ions within the ion trap utilize pressure regulators and fixed restrictors in order to control the flow of gas into the mass spectrometer. Since the overall throughput of a damping gas, such as helium, into the trap is in the order of 0.3 cc/min, the time required to eliminate absorbed water vapor due to the large surface area and void volume of regulator diaphragms, plumbing, etc. can be several weeks when first installing and/or starting a mass spectrometer. Furthermore, the hardware employed adds to the cost of the delivery apparatus.

OBJECTS AND SUMMARY OF THE INVENTION

It is a general object of the present invention to provide an improved apparatus and method for delivering dry collisional damping gas into the analyzing region of a mass spectrometer.

It is another object of the present invention to provide an apparatus which is continuously purged.

It is a further object of the present invention to provide an apparatus for delivering damping gas to a mass spectrometer which is simple and inexpensive.

There is provided a collisional gas delivery apparatus which includes a first capillary restrictor of a first internal diameter adapted to have one end connected to a source of pressurized damping gas, a second capillary having a second larger internal diameter having one end connected to the other end of the first capillary, and its other end open to atmospheric pressure. A third capillary restrictor having a diameter less than that of the second capillary restrictor is connected to the common end of the first and second capillary restrictor with its other end adapted for connection to the analyzing region of the mass spectrometer.

BRIEF DESCRIPTION OF THE DRAWINGS

The foregoing and other objects of the invention will be more clearly understood from the following description when read in connection with the accompanying drawing of the invention.

DESCRIPTION OF THE INVENTION

The collisional gas delivery apparatus includes a first capillary 11 which acts as a flow restrictor (hereinafter "capillary restrictor"). One end is connected to a fitting 12 for connection to a source of dry collisional damping gas such as helium. Its other end is connected to a suitable T connector 13 which receives a second capillary 14 which may have a diameter and length such that the gas flow restriction is less than that of the first capillary restrictor, and vented through connector 16 to atmospheric pressure. The third leg of the T connector 13 is connected to a capillary restrictor 17 with its other end adapted for connection to the mass spectrometer system 18 for supplying collisional damping gas to the mass spectrometer. The flow of collisional gas into the mass spectrometer is controlled by appropriately selecting the diameter and length of the third capillary restrictor 17. The flow depends upon the difference in pressure between the ends of the capillary restrictor 17. One end is essentially at zero pressure, while the other end is at atmospheric pressure. The pressure in the mass spectrometer has negligible effect upon the flow. Since temperature and atmospheric pressure in a laboratory environment change marginally over time, the flow rate of collisional gas is substantially constant. The second capillary has a substantially greater diameter whereby the typical flow rate is at least one order of magnitude higher than the flow rate through the third capillary restrictor, thereby permitting a rapid purge apparatus. No additional expense of a regulator is necessary in view of the fact that the atmospheric back pressure regulates the flow of damping gas through the third capillary 17 into the mass spectrometer.

By way of example, the capillary tubes selected in a particular embodiment for the delivery of 0.3 cc/min to the mass spectrometer were as follows: capillary tubes 11 and 14 had identical lengths of 8.5 cm with 0.050 mm internal diameter capillary tube 13 was 30 cm long with 0.25 mm internal diameter, and the pressure of the helium gas delivered to the first capillary restrictor 11 was between 60 and 100 psig.

Since the flow through restrictors varies as the fourth power of the internal diameter, the actual internal diameter of the capillary tubes must be determined in order to select a proper length to provide the desired flow. The stated internal diameter from vendors is "nominal" which cannot be relied upon for accuracy. The exact internal diameter of the vent capillary tube is not required. However, the internal diameter of the other capillary tubes should be determined to thereby select a proper length for a given flow rate of collisional gas. One method would be to select a given length of a capillary tubing and supplying helium to one end at a given pressure, for example 100 psi, at a selected ambient temperature, for example 25° C. The flow is then measured using a calibrated flow meter. The tubing internal diameter can then be determined from calculations or from a table. The appropriate length of tubing for a selected flow rate can then be determined.

Thus, there has been provided a simple apparatus for delivering dry collisional damping gas to the analyzing region of mass spectrometers. This is achieved with the elimination of regulators and other plumbing and the use of delivery tubing which has small surface area. The apparatus is continuously purged by the continuous flow of gas to the atmosphere. The flow is regulated by the atmospheric back pressure. Alternatively, if pressure greater than atmospheric pressure is required on capillary restrictor 17 for increased gas flow into the mass spectrometer, a back-pressure regulator vented to atmosphere may be added in place of capillary restrictor 14 or in addition to capillary restrictor 14 at fitting 16.

The foregoing descriptions of specific embodiments of the present invention are presented for the purposes of illustration and description. They are not intended to be exhaustive or to limit the invention to the precise forms disclosed;

obviously many modifications and variations are possible in view of the above teachings. One embodiment was chosen and described in order to best explain the principles of the invention and its practical applications, and to thereby enable others skilled in the art to best utilize the invention with modifications as are suited to the particular use contemplated. It is intended that the scope of the invention be defined by the following claims and their equivalents.

What is claimed is:

1. A collisional gas delivery apparatus for delivering collisional gas to a mass spectrometer whereby no gas flow meter is being used comprising:

a first capillary tube of a first internal diameter and length adapted to have one end connected to a source of damping gas, a second capillary tube having a diameter and length such as to present a substantially lower restriction to flow than the first capillary tube has one end connected to the other end of the first capillary tube, and its other end vented to the atmosphere whereby collisional gas can continuously flow from the source of damping gas to the atmosphere, a third capillary tube having a predetermined internal diameter and length has one end connected to the common ends of the first and second capillary tubes, and its other end adapted to be connected to the mass spectrometer.

2. A collisional gas delivery apparatus as in claim 1 in which the diameter and length of said third capillary tube is selected to deliver damping gas to said mass spectrometer at a predetermined flow rate when one end is at atmospheric pressure and the other end is at the mass spectrometer pressure.

3. The method of delivery of collisional gas to a mass spectrometer which comprises connecting the mass spectrometer to a continuously flowing stream of collisional gas at atmospheric pressure by a capillary restrictor of predetermined internal diameter and length.

* * * * *